United States Patent [19]

Gurstein et al.

[11] Patent Number: 4,803,466
[45] Date of Patent: Feb. 7, 1989

[54] CLEANING MACHINE FOR CARPET, UPHOLSTERY AND DRAPERIES

[75] Inventors: Bernard Gurstein, Canoga Park; Russell S. Gurstein, Agoura Hills, both of Calif.

[73] Assignee: U.S. Products, Inc., Agoura Hills, Calif.

[21] Appl. No.: 95,302

[22] Filed: Sep. 11, 1987

[51] Int. Cl.$^4$ .............................................. G08B 21/00
[52] U.S. Cl. .................................. 340/603; 15/319; 219/327; 340/540
[58] Field of Search .................. 340/603, 540; 15/319, 15/320; 219/209, 308, 327

[56] References Cited

U.S. PATENT DOCUMENTS

| | | | |
|---|---|---|---|
| 1,539,039 | 5/1925 | Blanding | 219/301 |
| 2,879,372 | 3/1959 | Dammond | 219/309 |
| 3,485,245 | 12/1969 | Lahr et al. | 604/114 |
| 4,112,538 | 9/1978 | Bates | 15/321 |
| 4,207,649 | 6/1980 | Bates | 15/319 |
| 4,308,636 | 6/1982 | Davis | 15/321 |
| 4,336,627 | 6/1982 | Bascus | 15/321 |
| 4,443,909 | 4/1984 | Cameron | 15/320 |
| 4,721,950 | 1/1988 | Andrejasich et al. | 340/603 |
| 4,728,941 | 3/1988 | Andrejasich | 340/603 |

*Primary Examiner*—Glen R. Swann III
*Attorney, Agent, or Firm*—Browdy & Neimark

[57] ABSTRACT

A cleaning machine for carpet, upholstery, draperies, and the like is designed with a safety system to prevent the cleaning liquid from being inadvertently overheated. The system senses the electrical conductivity or the density of the liquid and then limits the heating to a temperature which has been programmed to correspond that conductivity or density.

8 Claims, 2 Drawing Sheets

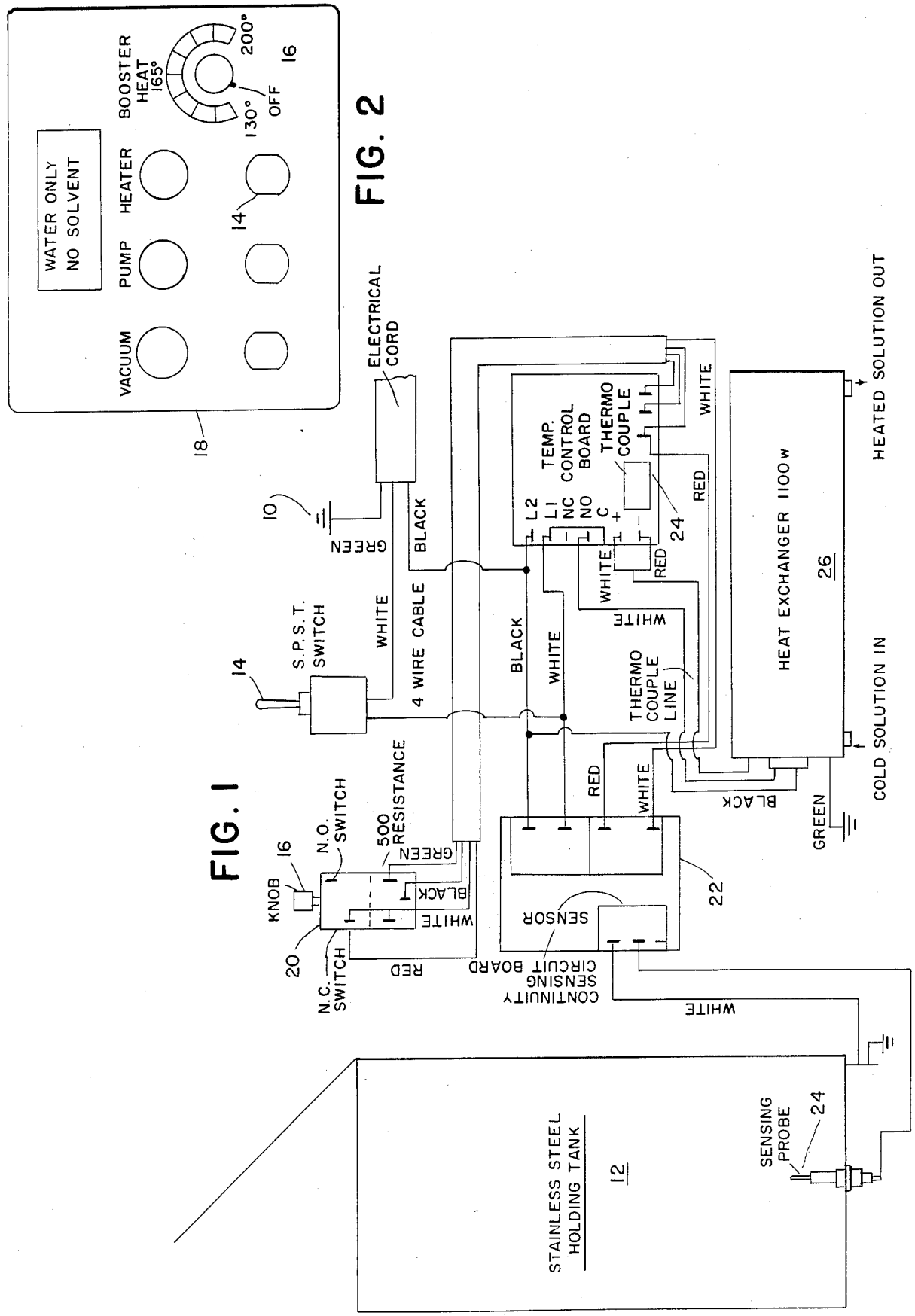

CLEANING MACHINE FOR CARPET, UPHOLSTERY AND DRAPERIES

BACKGROUND OF THE INVENTION

1. Field of the Invention

This invention relates to machines for cleaning carpets, draperies, upholstery, and the like and finds particular application in such machines where hot cleaning liquids are sprayed onto the surface and then removed by suction.

2. Description of the Prior Art

The prior art includes various types of cleaning machines with various types of liquid heating apparatus. In a common type of system, two general types of cleaning liquids can be used in the same machine: aqueous detergent cleaning solutions which can safely be heated to 200° F. and mineral spirit cleaning solvents which can become dangerously volatile at various lower temperatures depending upon the composition and concentration.

Because this type of fabric cleaning device works best when the liquid is at the highest temperature possible, it becomes necessary to operate the machine at different temperatures for different cleaning liquids. An aqueous-based detergent may be safely and effectively heated to a temperature of 200° F., but it is extremely dangerous to attempt heating a mineral spirits solution with a flash point of 140° F. to that temperature. Clearly there is a need for temperature limiting devices.

Prior art cleaning machines usually provide either a manually operated switch to choose between a finite number of temperatures or a manually operated dial from which any temperature in a range can be selected. While these machines are adequate if used correctly, it is possible that a machine operator sometimes using solvents and sometimes aqueous-based detergents in the same machine may inadvertently attempt to heat the solvent to an unsafe temperature.

SUMMARY OF THE INVENTION

It is the object of the present invention to eliminate the possibility of heating the liquid to an unsafe temperature as a result of operator error. This objective is accomplished by placing a fail-safe switching system in the machine. This system will prevent a non-aqueous, e.g., mineral spirits, solvent cleaning liquid from being overheated even when the operator inadvertently selects too high a temperature.

More specifically, this system employs one or more sensors that determine the nature of the liquid being used as the cleaning solution. For example, the nature of the liquid can be determined based on its conductivity by attempting to pass a small amount of electricity in the sensors. The cleaning machine will be preprogrammed to identify the maximum allowable temperature based on various conductivities. Alternatively, the nature of the liquid may be determined based on its density. Aqueous-based detergents are both denser and more conductive than mineral spirits solvent, which are relatively non-conductive.

In the preferred embodiment of the machine, the sensors determine whether an electrically conductive liquid (such as aqueous based detergent solution) is used as the cleaning liquid or whether an electrically non-conductive liquid (such as mineral spirits solvent) is being used. If the solution is conductive, then the sensors will allow the heating system to raise the temperature, typically as high as 200° F. If the solution is non-conductive, the sensors will limit the heating to a lower temperature, typically about 125° F.

If the operator attempts to operate the machine with the non-conductive liquid at a temperature above 125° F., the sensor functions as a safety device by shutting off part or all of the machine.

DESCRIPTION OF THE DRAWINGS

FIG. 1 is a schematic of an electrical circuit of one embodiment of the present invention.

FIG. 2 is a front view of a switch plate used in one embodiment of the present invention.

DETAILED DESCRIPTION OF THE PREFERRED EMBODIMENT

As shown in the drawings

Figure 3:
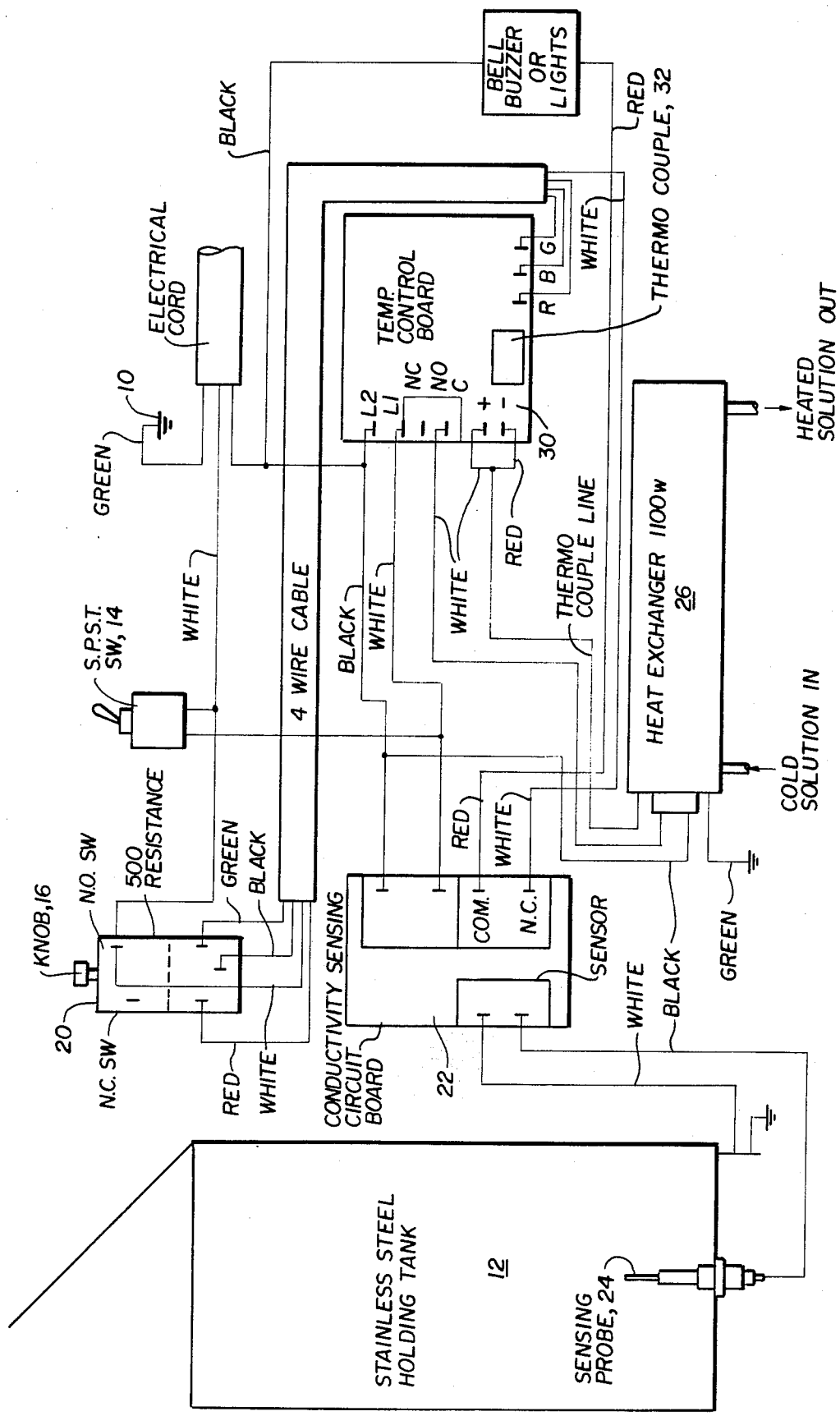
FIG. 3 is a schematic of an electrical circuit of another embodiment of the invention.

One embodiment of the present invention is a cleaning machine system 10 shown in FIG. 1. The system 10 includes a holding tank 12 which can contain either aqueous-based detergents which can be safely heated to 200° F. or non-aqueous solvents which would become unsafe at lower temperatures, for example 140° F. Both the heating switch 14 and the booster heating switch 16 are located on the switch plate 18 shown in FIG. 2. The solvents are heated by turning on heater switch 14 while leaving booster heating switch 16 off as shown in FIG. 2. In this mode, circuit board 22 is bypassed by the normally closed switch built into potentiometer 20 resulting in the solvent being heated to a safe temperature, possibly 125° F.

When an aqueous-based detergent is used, booster heating switch 16 can be turned to further heat the detergent to a higher temperature.

However, it is possible that booster heater switch 16 may inadvertently be turned on causing a dangerous situation. This is prevented by the present invention. When booster heating switch 16 is turned on to further increase the temperature of the fluid, the normally closed switch built into potentiometer 20 is opened thereby causing the circuit to open. If an aqueous-based detergent is being used, then sensing probe 24 determines that the fluid is electrically conductive and relays that information to the circuit board 22. Circuit board 22 closes the circuit, thereby bypassing the normally closed switch on potentiometer 20, which allows the temperature control board 30 to heat the heat exchanger 26 to the desired temperature indicated on switch 16 on the potentiometer 20. Board 24 includes a thermocouple 32 to detect the temperature of the heat exchanger.

It is possible, however, that when solvents are being used, an inadvertent attempt may be made to use the booster heater. When booster heater switch 16 is turned on, the normally closed switch built into potentiometer 20 opens thereby causing the circuit to open. However, sensing probe 24 determines that the liquid in holding tank 12 is non-conductive and relays to the circuit board 22. Circuit board 22 then keeps the circuit open, causing temperature control board 30 to shut off, thus preventing the solvent from being heated further.

Figure 4:
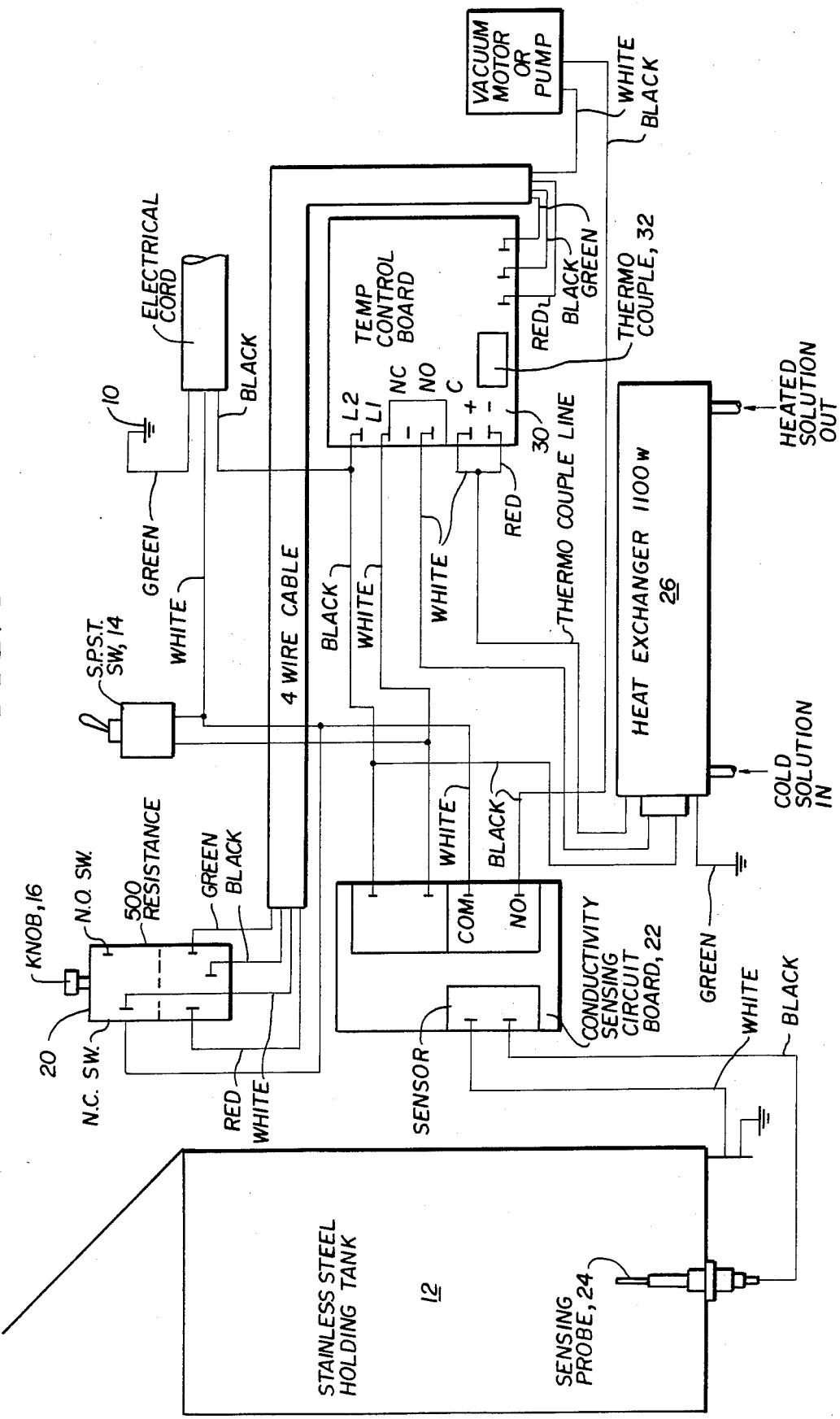
FIG. 4 is a schematic of an electrical circuit of another embodiment of the invention.

The present invention is by no means limited to the above embodiment. The system could measure other properties of the liquids including but not limited to the density of the liquids. The system could turn off all of the heating when a nonconductive liquid is used improperly. The system could turn off the pumping means or the vacuum means when a non-conductive liquid is being used improperly, and/or there could be audio or visual alarms signal an alert that an attempt is being made to overheat the solvent. FIG. 3 is an example of a circuit designed to set off an alarm when the solvent is overheated. FIG. 4 is an example of a circuit designed to shut off the pump or vacuum motor.

While certain specific embodiments have been disclosed in the foregoing description, it will be understood that various modifications within the scope of the invention may occur to those skilled in the art. Therefore, it is intended that adaptions and modifications should and are intended to be comprehended with the scope of the appended claims.

What is claimed is:

1. A cleaning machine comprising, in combination, a liquid holding means; sensing means within said holding means for determining whether a liquid in said holding means is aqueous or non-aqueous, said sensor providing input to a signal providing means for providing one signal when said liquid is aqueous and a different signal when said liquid is non-aqueous; heating means in fluid communication with said holding means; means for limiting the maximum temperature to which said heating means can raise said liquid, said limiting means receiving input from said signal providing means and being in electrical communication with said heating means, said maximum temperature significantly varying according to said signal received from said signal providing means.

2. The cleaning machine defined in claim 1, further comprising a switch in electrical communication with said signal providing means for automatically shutting off said heating means when an attempt is made to operate the machine at a temperature which is higher than said maximum temperature.

3. The cleaning machine of claim 1, wherein said sensing means determines the electrical conductivity of the liquid in the tank by attempting to pass a current therethrough.

4. The cleaning machine defined in claim 3 further comprising an audible or visual signal means which is activated when an attempt is made to operate the machine at a temperature higher than said maximum temperature.

5. The cleaning machine defined in claim 1 further comprising a vacuum motor; a switching means for automatically shutting off said vacuum motor when an attempt is made to operate the machine at a higher temperature than said maximum temperature.

6. The cleaning machine defined in claim 1 wherein said maximum temperature is higher for a conductive liquid than for a non-conductive liquid.

7. A method of heating a liquid used in a cleaning machine comprising the steps of sensing the electrical conductivity of said liquid by means of a sensing means in contact with said liquid; generating a signal, the characteristics of which vary according to the electrical conductivity of said liquid sensed by said sensing means; heating said liquid; limiting the maximum temperature to which said liquid is heated to a temperature which varies according to the said variation in characteristics of said signal.

8. A cleaning machine comprising, in combination, a liquid holding means; sensing means within said holding means responsive to the density of a liquid in said holding means for providing a signal the characteristics of which significantly vary according to the density of said liquid; heating means in fluid communication with said holding means; means for limiting the maximum temperature to which said heating means can raise said liquid, said limiting means receiving said signal generated by said sensing means and being in electrical communication with said heating means, said maximum temperature significantly varying in response to said variations in said signal.

* * * * *